United States Patent

Raupach et al.

(10) Patent No.: US 7,599,464 B2
(45) Date of Patent: Oct. 6, 2009

(54) METHOD AND COMPUTED TOMOGRAPHY SYSTEM FOR PRODUCING TOMOGRAMS OF AN OBJECT

(75) Inventors: Rainer Raupach, Adelsdorf (DE); Otto Sembritzki, Wachenroth (DE)

(73) Assignee: Siemens Aktiengesellschaft, Munich (DE)

( * ) Notice: Subject to any disclaimer, the term of this patent is extended or adjusted under 35 U.S.C. 154(b) by 743 days.

(21) Appl. No.: 11/377,671

(22) Filed: Mar. 17, 2006

(65) Prior Publication Data

US 2006/0235293 A1 Oct. 19, 2006

(30) Foreign Application Priority Data

Mar. 18, 2005 (DE) .................. 10 2005 012 654

(51) Int. Cl.
*A61B 6/03* (2006.01)
(52) U.S. Cl. .................. 378/4; 378/19; 378/901
(58) Field of Classification Search .................. 378/4, 378/19, 901; 382/128–131
See application file for complete search history.

(56) References Cited

U.S. PATENT DOCUMENTS

| | | | |
|---|---|---|---|
| 5,265,142 A * | 11/1993 | Hsieh | ................ 378/4 |
| 5,513,236 A | 4/1996 | Hui | |
| 5,907,593 A | 5/1999 | Hsieh et al. | |
| 2004/0240719 A1 | 12/2004 | Gruebnau et al. | |
| 2005/0190984 A1 | 9/2005 | Fischer et al. | |

FOREIGN PATENT DOCUMENTS

| | | |
|---|---|---|
| DE | 195 47 277 A1 | 7/1996 |
| DE | 103 05 221 A1 | 2/2003 |
| DE | 103 20 882 A1 | 12/2004 |

OTHER PUBLICATIONS

Tischenko et al., Reduction of Anatomical Noise in Medical X-ray Images, Apr. 22, 2004, Proceedings of the Second Malmo Conference on Medical X-ray Imaging, Radiation Protection Dosimetry, vol. 114, Nos. 1-3, pp. 69-74.*

Tischenko et al., Evaluation of a Novel Method of Noise Reduction using Computer-Simulated Mammograms, Apr. 22, 2004, Proceedings of the Second Malmo Conference on Medical X-ray Imaging, Radiation Protection Dosimetry, vol. 114, Nos. 1-3, pp. 81-84.*

(Continued)

*Primary Examiner*—Edward J Glick
*Assistant Examiner*—John M Corbett
(74) *Attorney, Agent, or Firm*—Harness, Dickey & Pierce, P.L.C.

(57) ABSTRACT

A method and a computed tomography system are disclosed for producing computed tomograms of an object. A set of detector output data that represent beams over a specific angular range and a scan of a specific subregion of the object, are divided into m≧2 complete partial detector output data records that respectively cover the same complete angular range, but are reduced with their sampling density by 1/m and have mutually independent data records. Intermediate image data records (m records) that represent the identical object region are reconstructed from the m complete partial detector output data records. A correlation analysis is carried out between the m intermediate image data records. Finally, an image data record is produced that consists only of correlated data and includes no uncorrelated data.

19 Claims, 4 Drawing Sheets

OTHER PUBLICATIONS

Tischenko et al., An artifact-free structure-saving noise reduction using the correlation between two images for threshold determination in the wavelet domain, Feb. 17, 2005, Proceedings of Medical Imaging 2005: Image Processing, SPIE vol. 5747, pp. 1066-1075.*

Hoeschen et al., Testing a wavelet based noise reduction method using computer-simulated mammograms, Feb. 13, 2005, Proceedings of Medical Imaging 2005: Physics of Medical Imaging, SPIE vol. 5745, pp. 969-977.*

Hoeschen et al., Separating the uncorrelated noise from the correlated detector noise of flat panel systems in order to quantify flat panel noise easily, Feb. 13, 2005, Proceedings of Medical Imaging 2005: Physics of Medical Imaging, SPIE vol. 5745, pp. 51-60.*

* cited by examiner

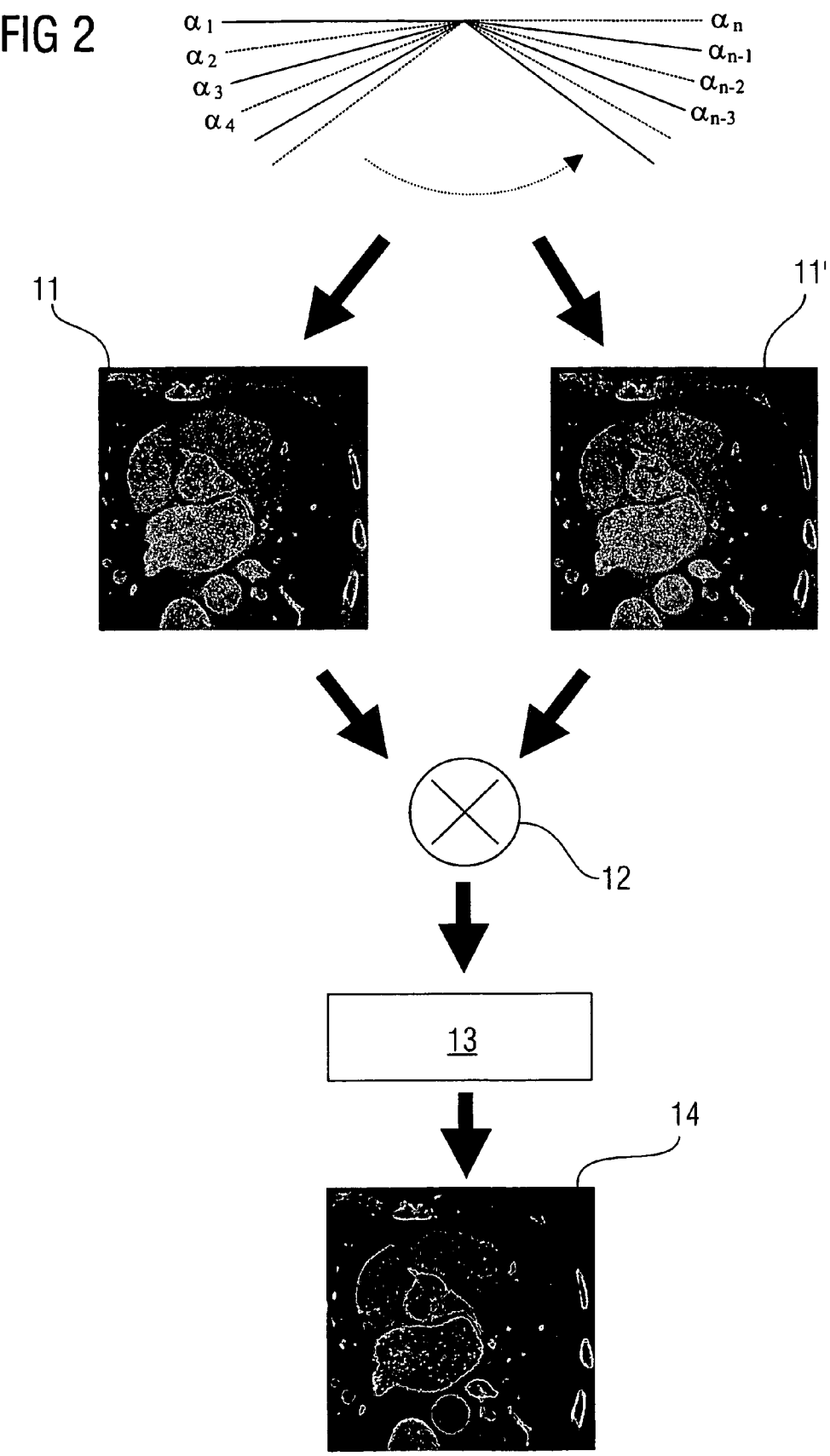

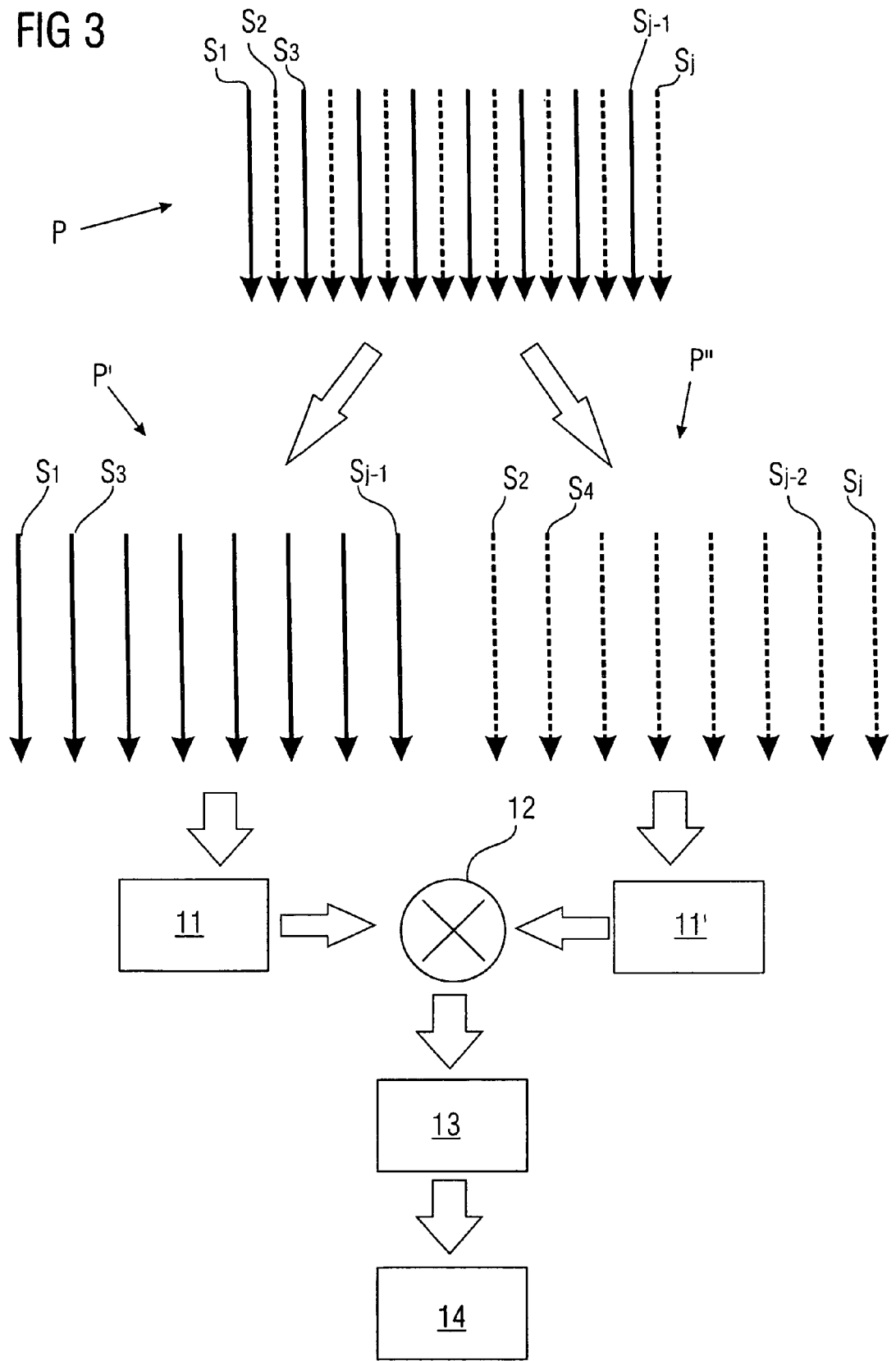

METHOD AND COMPUTED TOMOGRAPHY SYSTEM FOR PRODUCING TOMOGRAMS OF AN OBJECT

The present application hereby claims priority under 35 U.S.C. §119 on German patent application number DE 10 2005 012 654.5 filed Mar. 18, 2005, the entire contents of which is hereby incorporated herein by reference.

FIELD

The invention generally relates to a method and/or computed tomography system for producing computed tomograms of an object, such as, for example, a patient. For example, it may relate to one or the other in which, in order to scan the object, at least one X-ray tube rotates relative to the object about the latter and about a system axis. At least one detector, for example at least one multirow detector, may be used for detecting the attenuation of the X-radiation during the rotation of the at least one X-ray tube and outputting it as detector output data to a control and arithmetic unit. Finally, computed tomograms may be reconstructed from these detector output data. Either two-dimensional tomograms of the object or volume data records can be involved in this case.

BACKGROUND

Methods are generally known in multifarious variations, it being possible in principle to distinguish between 2D and 3D reconstruction methods, and these methods are used in essence for patient diagnostics. Because of the ionizing property of the radiation used for the purpose of scanning the patient, and of the risk accompanying it with reference to cell generation, the concern when using these methods is always to carry out the examinations at the lowest possible dose. Owing to this low available dose as the patient is being scanned, the quantum noise present becomes highly relevant to image quality and impairs the image quality.

In order to improve the image quality, it is proposed in part to use nonlinear image filters that, by contrast with simple linear methods, can reduce the noise without impairing edges of objects included in the image. Usually, such intelligent filters use the image properties in the two- or three-dimensional environment of the respective pixel in order, firstly, to determine the position of edges and, subsequently to apply suitable filters, for example in a fashion parallel to detected edges.

Such a method is described, for example, in patent application DE 10 2004 008 979.5-53 from Siemens. Such a method for noise reduction has, however, the following disadvantage:

If the filter is executed in only one step, the spatial range must be sufficiently large in order to implement an adequate low-pass action. However, this raises the risk of impairing small structures. If it is desired to keep the range of the filters as small as possible and yet to reduce the noise effectively, recourse must be made to iterative methods that are problematical in practical use with regard to performance and because of the restricted computational capacity.

Another possibility for reducing quantum noise is described, for example, in laid-open patent application DE 103 05 221 A1, the entire contents of which are hereby incorporated herein by reference. The disclosure content of this document is hereby incorporated fully into the present patent application. This document exhibits a method for reducing noise structures in two- or three-dimensional images, the same object being recorded under identical geometrical conditions or ones that are changed in a defined way, a transformation of the images produced subsequently being carried out in a frequency domain, and frequency-dependent correlations being sought by decomposing the images into a number of frequency bands, and a new image being back-transformed again exclusively from the frequency-dependent correlations. As a result, the uncorrelated noise components of the image are left behind, and the newly produced retransformed image includes only correlated image components, that is to say components that are to be ascribed to actual object structures.

SUMMARY

It is an object of at least one embodiment of the invention to find a method and/or a computed tomography system that likewise removes the quantum noise from computed tomography displays, the aim being, however, to dispense with the requirement of two temporally or spatially offset pictures.

The inventors have recognized that it is also possible to obtain images that are statistically independent of one another with reference to quantum noise, or three-dimensional image information when the data of a scanning pass are divided homogeneously over a number of data records, images or volume data records are reconstructed from these data records, and these images or volume data records are subsequently subjected to a correlation analysis, uncorrelated image components being suppressed, and the images themselves being produced in turn from the correlated image components that must then include the object structures actually present. For example, it is possible here to use cross-correlation functions in the spatial domain or wavelet coefficients in order to determine the correlation between the data records.

Thus, it is no longer necessary to carry out temporally offset or spatially offset scannings, but rather the total sum of the data can be obtained during a single scan, all that is required being a homogeneous division of the data into complete partial data records. The data records are complete whenever they cover the same angular range, partial data records because they include only a portion of the overall data material to hand, and the sum of the partial data records again yields the total data record, it not being permissible for there to be any redundancy between the individual partial data records so that data statistically independent of one another are present in the individual partial data records.

The inventors propose in accordance with this basic idea a method for producing computed tomograms of an object, for example a patient, having at least the following method steps:

in order to scan the object at least one X-ray tube is rotated relative to the object about the latter and about a system axis, at least one detector, preferably at least one multirow detector, detects the attenuation of the X-radiation during the rotation of the at least one X-ray tube and outputs it as detector output data to a control and arithmetic unit, a set of detector output data that represent beams over a specific angular range and scan a specific subregion of the object are divided into $m \geq 2$ complete partial detector output data records that respectively cover the same complete angular range, but are reduced with their sampling density by 1/m and have mutually independent data records, m intermediate image data records that represent the identical object region are reconstructed from the m complete partial detector output data records, a correlation analysis is carried out between the m intermediate image data records, and an image data record is produced that consists only of correlated data and includes no uncorrelated data.

It is certainly possible in principle to use more than two partial detector output data records and to produce two intermediate image data records, but the optimum is when exactly two intermediate image data records are produced and the correlation analysis is applied therefor.

It is advantageous, moreover, when the intermediate images are transformed for the purpose of correlation analysis such that the image information is present in a number of frequency bands, the latter are intercompared, and an image is retransformed exclusively with the aid of correlated data.

For example, a cross-correlation method is carried out for the purpose of correlation analysis between the m intermediate image data records.

Furthermore, a wavelet transformation can be carried out over the intermediate image data records for the purpose of correlation analysis between the m intermediate image data records, and the correlation can be assessed with the aid of identical or different wavelet coefficients.

In a particular application of at least one embodiment of the method, the latter can be carried out during the calculation of tomograms in such a way that a complete set of n projections with the projection angles $\alpha_1$ to $\alpha_n$ is divided into m complete partial projection sets, each partial projection set including each m-th projection angle, beginning in each case with another consecutive projection angle, an intermediate tomogram being constructed from each partial projection set, correlation analysis being carried out with reference to the m intermediate tomograms, and a tomogram being back-calculated from the correlated data.

In another variant of the tomogram calculation, a complete set of n projections with the projection angles $\alpha_1$ to $\alpha_n$ and representing beams $S_1$ to $S_j$ parallel to each individual projection P can be divided into m complete partial projection sets, each partial projection set including all the projection angles $\alpha_1$ to $\alpha_n$, but representing only the data of each m-th parallel beam, an intermediate tomogram being reconstructed from each partial projection set, the correlation analysis being carried out with reference to the m intermediate tomograms, and subsequently a tomogram being back-calculated from the correlated data.

If volume data records are calculated instead of tomograms, the method can be used to the effect that a complete set of n projections with the projection angles $\alpha_1$ to $\alpha_n$ and representing beams $S_1$ to $S_j$ parallel to each individual projection P is divided into m complete partial projection sets, each partial projection set including all the projection angles $\alpha_1$ to $\alpha_n$, but representing only the data of each m-th parallel beam, an intermediate tomogram being reconstructed from each partial projection set, the correlation analysis being carried out with reference to the m intermediate tomograms, and a tomogram being back-calculated from the correlated data.

It is advantageous, furthermore, when m volume data records are reconstructed from m complete partial detector output data records, the correlation analysis being carried out with reference to the m volume data records, and a volume data record being back-calculated from the correlated data.

Furthermore, it is advantageous when during scanning of the object by use of a multi-row detector the detector output data of detector elements arranged like a chessboard are combined to form two complete partial detector output data records such that each detector element corresponding to a "white" field is assigned to a first partial detector output data record, and each detector element corresponding to a "black" field is assigned to a second partial detector output data record, at least one intermediate image is reconstructed from each partial detector output data record obtained in such a way, the correlation analysis is subsequently carried out in relation in each case to two intermediate images with temporally and spatially identical object scanning, and an image data record is calculated from correlated data.

At least one embodiment of the above-described method can be applied, on the one hand, to the calculation of complete images or volume data that correctly represent the object structure, but it is also possible to apply the method according to at least one embodiment of the invention to so-called incomplete tomograms or volume data, as is known from the SMPR method, for example. The angular range can accordingly on the one hand cover at least 180° from which the set of detector output data to which the method according to at least one embodiment of the invention is applied originates.

On the other hand, it is also possible that the angular range merely covers a segment smaller than 180° and in order to produce a final image data record so many image data records are added up that they cover overall an angular range of at least 180°. Thus, at least one embodiment of the described method of suppressing the quantum noise can be used not only on images that visualize the object structure, but also on so-called incomplete data records that do not become complete and recognizable images until a number of incomplete image data records that yield less than 180° overall are added up.

The method according to at least one embodiment of the invention can be used, moreover, both in conjunction with spiral scanning and in conjunction with sequential scanning.

Moreover, the inventors also propose at least one embodiment of a computed tomography system for producing computed tomograms of an object, for example a patient, having an apparatus for rotating scanning of the object having at least one X-ray tube and at least one detector that continually detects the attenuation of the X-rays and outputs it to a control and arithmetic unit as detector output data. A system including at least one arithmetic unit and programs or program modules may be integrated, that during operation carries out the above-described method steps of at least one embodiment.

Additional features and advantages of the invention emerge from the following description of example embodiments with reference to the drawings.

BRIEF DESCRIPTION OF THE DRAWINGS

Embodiments of the invention are described in more detail below with reference to the example embodiments in the description and the figures, it being pointed out that only the elements essential to the immediate understanding of the embodiments of invention are shown. The following reference symbols are used here: 1: computed tomography system; 2: X-ray tube; 3: detector; 4: system axis; 5: scanning apparatus; 6: displaceable patient couch; 7: patient; 8: opening in the scanning device; 9: control and arithmetic unit; 10: control and data line; 11, 11': intermediate images; 12: determination of correlated components; 13: synthesis of correlated components; 14: denoised image; 15, 15': intermediate volume data records; 16: denoised volume data records; P: complete projection; P', P": complete partial projections; $Prg_1$-$Prg_n$: programs/program modules; S: complete set of beams through a voxel; $S_x$: beams; S', S": complete partial set of beams; V: voxel; $\alpha_1$ to $\alpha_n$: angles.

In detail:

FIG. 2 shows a schematic of the method according to an embodiment of the invention with reference to a tomogram calculation by way of complete projection sets;

FIG. 3 shows the division of a parallel projection into two complete partial parallel projections;

DETAILED DESCRIPTION OF THE EXAMPLE EMBODIMENTS

Figure 1:
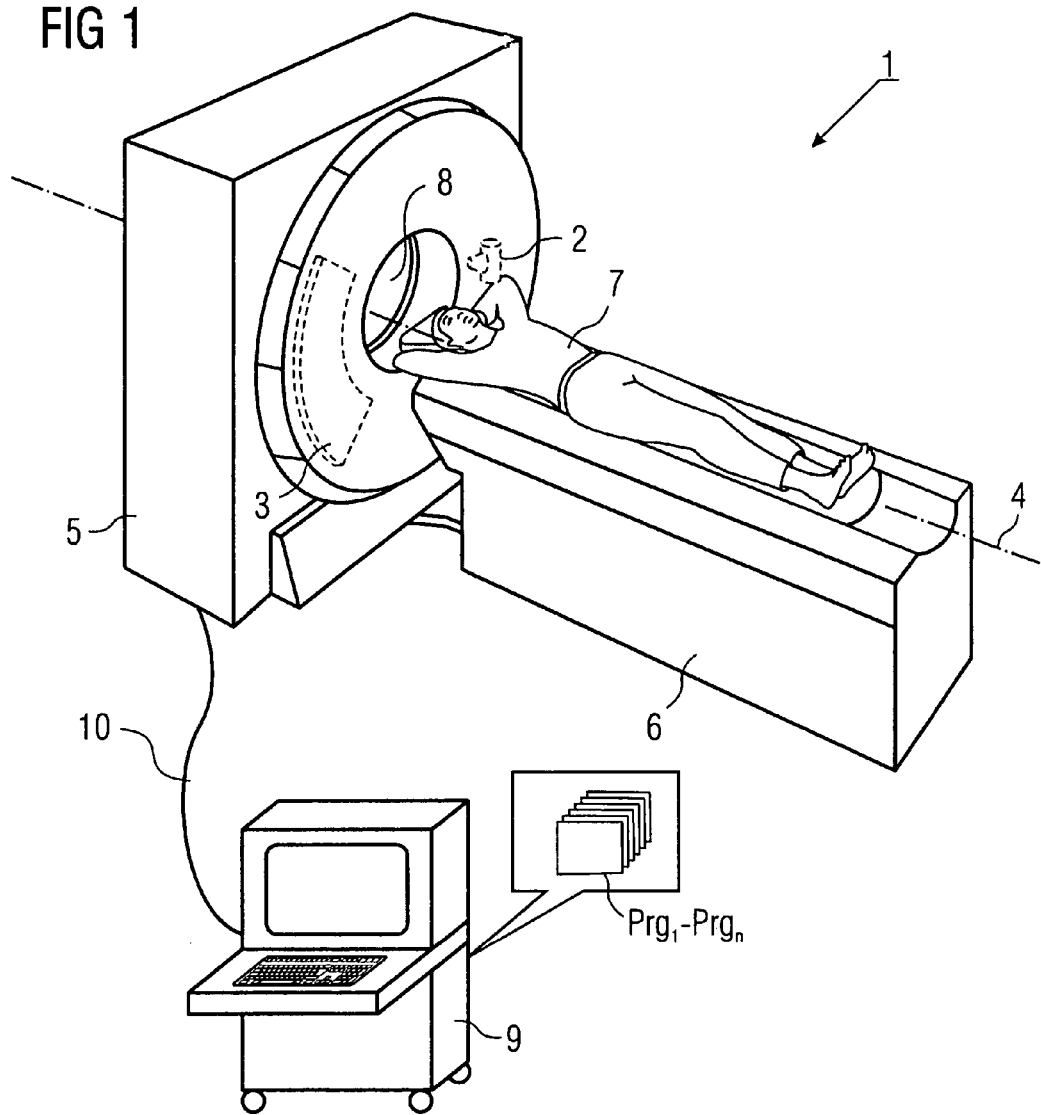
FIG. 1 shows a schematic of a computed tomography system for carrying out the method according to an embodiment of the invention.

FIG. 1 shows a schematic of a computed tomography system 1 including the scanning system 5, which has a gantry with an X-ray tube 2 arranged thereon and a detector 3 situated opposite. Located between the X-ray tube 2 and the detector 3 is an opening 8 into which a patient 7 who is arranged on a moveable patient couch 6 can be pushed through the opening 8 along the system axis 4 and can be scanned in the process.

The computed tomography system is controlled by a control and arithmetic unit 9 that is connected via a control and data line 10 to the scanning system 5 and also controls the feed of the patient couch 6. The detector output data, which are recorded with the aid of the detector 3 as the patient 7 is being scanned, are led to the computer 9 by the control and data line 10 and reconstructed there, or if appropriate in another computer system, with the aid of computer programs such that it is possible to output a tomogram or volume display for the patient on a display screen of the computer.

FIG. 2 illustrates a variant of the method, in which from a complete set of n projections over the n projection angle $\alpha_1$ to $\alpha_n$ of an identical slice two have been recorded. These n projections are denoted in FIG. 2 at the top by the angles $\alpha_1$ to $\alpha_n$. Two complete subsets of projections are formed from all these angles of the parallel projections $\alpha_1$ to $\alpha_n$, which are to be illustrated here in digital fashion without restriction of generality, the projections with odd indices being recorded in a first subset of the projections, and the projections with even indices being recorded in a second complete subset of projections. Intermediate tomograms 11 and 11' are reconstructed on the two projections, as illustrated by the arrows pointing left and right. Subsequently, as illustrated by symbol 12, the correlated component between the tomograms is determined, the method step 13 is used to carry out a synthesis of the correlated components and a denoised image is thereby produced.

Another variant of the division of the existing detector data for the purpose of calculating intermediate images is indicated schematically in FIG. 3. It is shown here how a projection P that includes a multiplicity of detector data of parallel beams S1 to Sj is divided into two complete partial projections P' and P'''.

In this case, the data that originate from beams with odd indices are assigned to the projection P', and the data from beams with even indices are assigned to the complete partial projection P'''. This method is carried out for all projection angles $\alpha_1$ to $\alpha_n$ such that it is possible to reconstruct two intermediate images 11 and 11' from the projections. A finished image 14 is calculated or retransformed from these reconstructed intermediate images 11 and 11' via the correlation analysis 12 and subsequent synthesis of the correlated components 13.

Figure 4:
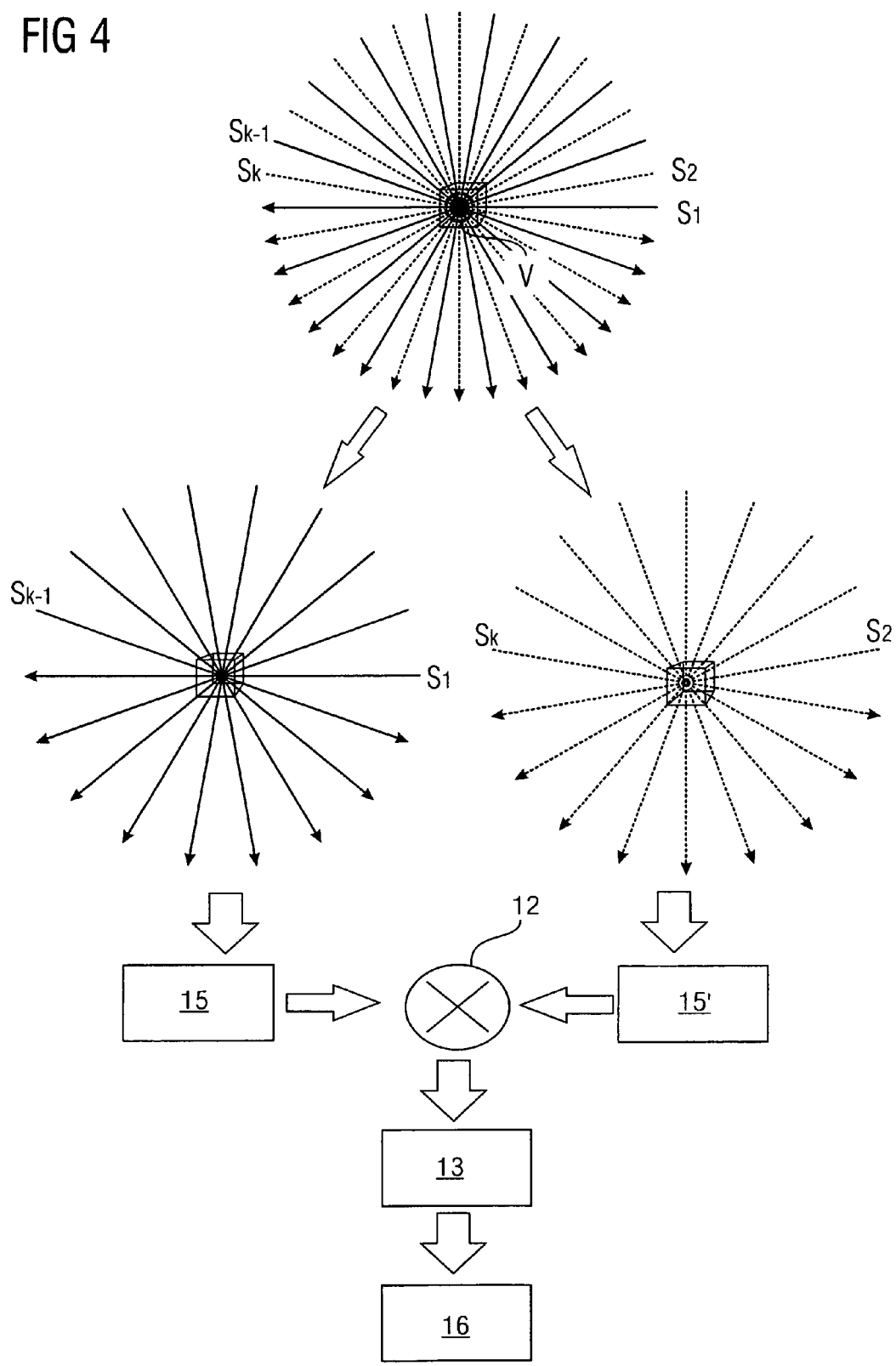
FIG. 4: shows the division of a voxel scan in accordance with the method according to an embodiment of the invention.

FIG. 4 shows by way of example the application of the method according to at least one embodiment of the invention to voxel-specific reconstructions. Displayed here are the beams S1 to Sk that penetrate a voxel V and correspond to a 180° half revolution. In the case of the voxel-wise reconstruction, the individual voxel values of an examination object are reconstructed from many sets of beams S of such type having beams that respectively penetrate a voxel.

As illustrated schematically in FIG. 4, the method according to at least one embodiment of the invention can also be applied here by dividing each set of beams S of a voxel V, more precisely the detector data record produced thereby, into complete partial data records that correspond to the sets of beams S' and S''. Volume data records 15 and 15' are then calculated in a voxelwise fashion from the sum of the complete partial detector data records corresponding to the partial sets of beams S' and S'', it is determined between these volume data records in method step 12 which components are correlated with one another, and a de-noised volume data record 16 is subsequently produced in method step 13 by a synthesis of the correlated components.

Figure 5:
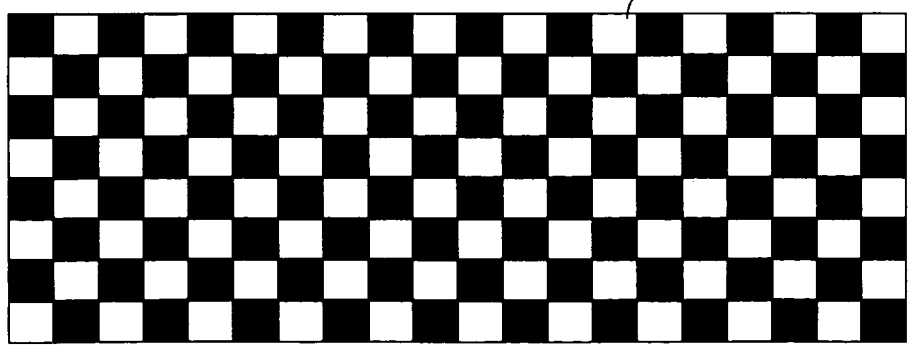
FIG. 5 shows a multirow detector with an arrangement of the detector elements in the form of a chessboard.

Another variant of the method according to at least one embodiment of the invention resides in that when scanning the examination object, for example a patient, the detector output data are divided immediately in accordance with a division of the individual detector elements of a multi-row detector in the manner of a chessboard, as illustrated schematically in FIG. 5. In this case, the detector data composed of detector elements offset in row-wise and column-wise fashion are respectively allocated to the two complete partial data records.

The multi-row detector illustrated is a multi-row detector that has a multiplicity of identical detector elements, the detector elements being drawn in the illustration as black or white detector fields in a fashion similar to a chessboard in order to distinguish their assignment. However, it is to be noted that embodiments of the invention are in no way restricted to detector elements of identical extent such as are shown here. According to at least one embodiment of the invention, there is then a division of the measured detector data into detector data that originate from white or black detector elements, it then being possible to carry out the subsequent reconstruction of the tomograms or volume data records in accordance with all reconstruction methods known per se. The result of this is two statistically mutually independent image data records that are capable, in turn, of being intercompared by way of a correlation method such that images that consist exclusively of correlated data can subsequently be calculated.

It may be pointed out once again that the concrete calculation of the correlated data of a number of images of the identical object is explained in the document DE 103 05 221 A1 cited above, and that this mode of calculation is fully incorporated by reference into the present application.

It goes without saying that the above named features of embodiments of the invention can be used not only in the combination respectively specified, but also in other combinations or on their own without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing an image data record of an object, comprising:
    rotating, in order to scan the object, at least one X-ray tube relative to the object;
    detecting, via at least one detector, an attenuation of X-radiation during the rotation of the at least one X-ray tube and outputting detector output data;
    dividing a set of detector output data, representing beams over a specific angular range and scanning a specific subregion of the object, into $m \geq 2$ complete partial detector output data records respectively covering a same complete angular range, but reduced with their sampling density by 1/m and including mutually independent data records;
    reconstructing m intermediate image data records, representing an identical object region, from the m complete partial detector output data records;
    carrying out a correlation analysis between the m intermediate image data records; and
    producing an image data record that includes only correlated data and that includes no uncorrelated data.

2. The method as claimed in claim 1, wherein exactly two complete partial detector output data records are formed.

3. The method as claimed in claim 2, wherein:
    during scanning of the object, using a multirow detector, the detector output data of detector elements arranged like a chessboard are combined to form two complete partial detector output data records such that each detector element corresponding to a "white" field is assigned to a first partial detector output data record, and each detector element corresponding to a "black" field is assigned to a second partial detector output data record,
    at least one intermediate image is reconstructed from each partial detector output data record obtained in such a way,
    the correlation analysis is subsequently carried out in relation in each case to two intermediate images with temporally and spatially identical object scanning, and
    an image data record is calculated from correlated data.

4. The method as claimed in claim 2, wherein the intermediate images are transformed, for correlation analysis, such that the image information is present in a number of frequency bands, the intermediate images being intercompared and the noiseless image data record being retransformed exclusively with the aid of at least one of correlated data of an intermediate image and a number of intermediate images.

5. The method as claimed in claim 2, wherein:
    a complete set of n projections with the projection angles $\alpha_1$ to $\alpha_n$ and representing beams $S_1$ to $S_j$ parallel to each individual projection P is divided into m complete partial projection sets, each partial projection set including all the projection angles $\alpha_1$ to $\alpha_n$, but representing only the data of each m-th parallel beam,
    an intermediate tomogram is reconstructed from each partial projection set,
    the correlation analysis is carried out with reference to the m intermediate tomograms, and
    a tomogram is back-calculated from the correlated data.

6. The method as claimed in claim 2, wherein:
    m volume data records are reconstructed from m complete partial detector output data records,
    the correlation analysis is carried out with reference to the m volume data records, and
    a volume data record is back-calculated from the correlated data.

7. The method as claimed in claim 1, wherein the intermediate images are transformed, for correlation analysis, such that the image information is present in a number of frequency bands, the intermediate images being intercompared and the noiseless image data record being retransformed exclusively with the aid of at least one of correlated data of an intermediate image and a number of intermediate images.

8. The method as claimed in claim 1, wherein a cross-correlation method is carried out for correlation analysis between the m intermediate image data records.

9. The method as claimed in claim 1, wherein a wavelet transformation is carried out over the intermediate image data records for correlation analysis between the m intermediate image data records, and the correlation is assessed with the aid of identical or different wavelet coefficients.

10. The method as claimed in claim 1, wherein:
    a complete set of n projections with the projection angles $\alpha_1$ to $\alpha_n$ is divided into m complete partial projection sets, each partial projection set including each m-th projection angle, beginning in each case with another consecutive projection angle,
    an intermediate tomogram is constructed from each partial projection set,
    the correlation analysis is carried out with reference to the m intermediate tomograms and
    a tomogram is back-calculated from the correlated data.

11. The method as claimed in claim 1, wherein:
    a complete set of n projections with the projection angles $\alpha_1$ to $\alpha_n$ and representing beams $S_1$ to $S_j$ parallel to each individual projection P is divided into m complete partial projection sets, each partial projection set including all the projection angles $\alpha_1$ to $\alpha_n$ but representing only the data of each m-th parallel beam,
    an intermediate tomogram is reconstructed from each partial projection set,
    the correlation analysis is carried out with reference to the m intermediate tomograms, and
    a tomogram is back-calculated from the correlated data.

12. The method as claimed in claim 1, wherein:
    m volume data records are reconstructed from m complete partial detector output data records,
    the correlation analysis is carried out with reference to the m volume data records, and
    a volume data record is back-calculated from the correlated data.

13. The method as claimed in claim 1, wherein the angular range covers at least 180°.

14. The method as claimed in claim 1, wherein the angular range covers a segment smaller than 180° and in order to produce a final image data record, so many image data records are added up that they cover overall an angular range of at least 180°.

15. The method as claimed in claim 1, wherein the method is used in conjunction with spiral scanning.

16. The method as claimed in claim 1, wherein the method is used in conjunction with sequential scanning.

17. The method as claimed in claim 1, wherein:
a complete set of n projections with the projection angles $\alpha_1$ to $\alpha_n$ is divided into m complete partial projection sets, each partial projection set including each m-th projection angle, beginning in each case with another consecutive projection angle,
an intermediate tomogram is constructed from each partial projection set,
the correlation analysis is carried out with reference to the m intermediate tomograms and
a computed tomogram is back-calculated from the correlated data.

18. A computer readable medium including program segments for, when executed on a computer, causing the computer to implement the method of claim 1.

19. A computed tomography unit for producing computed tomograms of an object, comprising:
an apparatus to rotate scanning of the object, including at least one X-ray tube and at least one detector to continually detect the attenuation of the X-rays and output the detected attenuation as detector output data; and
a system including at least one arithmetic unit and at least one of programs and program modules for, during operation,
dividing a set of detector output data, representing beams over a specific angular range and scanning a specific subregion of the object, into $m \geq 2$ complete partial detector output data records respectively covering a same complete angular range, but reduced with their sampling density by 1/m and including mutually independent data records,
reconstructing m intermediate image data records, representing an identical object region, from the m complete partial detector output data records,
carrying out a correlation analysis between the m intermediate image data records, and
producing an image data record that consists only of correlated data and includes no uncorrelated data.

* * * * *